(12) United States Patent
Kashani et al.

(10) Patent No.: US 8,478,612 B2
(45) Date of Patent: *Jul. 2, 2013

(54) SYSTEM AND METHOD OF PROVIDING AN OPTIMIZED-PERSONALIZED HEALTH MAINTENANCE PLAN

(75) Inventors: Mariam Kashani, Bethesda, MD (US); Marina Vernalis, Silver Spring, MD (US)

(73) Assignee: Dynamic Health Innovations, LLC, Bethesda, MD (US)

( * ) Notice: Subject to any disclaimer, the term of this patent is extended or adjusted under 35 U.S.C. 154(b) by 218 days.

This patent is subject to a terminal disclaimer.

(21) Appl. No.: 13/092,081

(22) Filed: Apr. 21, 2011

(65) Prior Publication Data

US 2011/0246227 A1    Oct. 6, 2011

Related U.S. Application Data

(63) Continuation of application No. 12/203,086, filed on Sep. 2, 2008, now Pat. No. 7,957,985.

(60) Provisional application No. 60/967,020, filed on Sep. 4, 2007.

(51) Int. Cl.
*G06Q 10/00* (2012.01)
*G06Q 50/00* (2012.01)

(52) U.S. Cl.
USPC .................................................. 705/3; 705/2

(58) Field of Classification Search
USPC ........................................................ 705/2, 3
See application file for complete search history.

(56) References Cited

U.S. PATENT DOCUMENTS

| | | | | |
|---|---|---|---|---|
| 5,951,300 | A | * | 9/1999 | Brown ........................ 434/236 |
| 6,032,119 | A | * | 2/2000 | Brown et al. ..................... 705/2 |
| 2002/0072933 | A1 | * | 6/2002 | Vonk et al. ....................... 705/2 |
| 2002/0082144 | A1 | * | 6/2002 | Pfeffer .............................. 482/8 |
| 2003/0028399 | A1 | * | 2/2003 | Davis et al. ...................... 705/2 |
| 2003/0120515 | A1 | * | 6/2003 | Geller .............................. 705/2 |
| 2004/0006488 | A1 | * | 1/2004 | Fitall et al. ...................... 705/2 |
| 2005/0060187 | A1 | * | 3/2005 | Gottesman ...................... 705/2 |
| 2006/0085217 | A1 | * | 4/2006 | Grace .............................. 705/1 |
| 2008/0147441 | A1 | * | 6/2008 | Kil .................................... 705/2 |
| 2008/0312510 | A1 | * | 12/2008 | Ross ............................ 600/300 |

* cited by examiner

*Primary Examiner* — Neal Sereboff
(74) *Attorney, Agent, or Firm* — Syndicated Law; Brian S. Boyer

(57) ABSTRACT

Systems and methods for providing an optimized-personalized health maintenance plan are presented. The teachings include a method for creating an iteratively-optimized, personalized health maintenance plan for a user. The method includes producing a recognized health profile for a subject, developing a first personalized health maintenance plan from the recognized health profile, and converting compiled information into a presentation format for the first personalized health maintenance plan, or an optimized-personalized health maintenance plan based on at least a first iterated questionnaire. The personalized health maintenance plan is optimized to increase the level of specificity of the personalized health maintenance plan for the user.

22 Claims, 13 Drawing Sheets

SYSTEM AND METHOD OF PROVIDING AN OPTIMIZED-PERSONALIZED HEALTH MAINTENANCE PLAN

CROSS-REFERENCE TO RELATED APPLICATIONS

This application is a continuation of U.S. patent application Ser. No. 12/203,086, filed Sep. 2, 2008, and claims the benefit of U.S. Provisional Application No. 60/967,020, filed Sep. 4, 2007, each application of which is hereby incorporated herein by reference in its entirety.

BACKGROUND

1. Field of the Invention

The teachings are directed to a method for creating an iteratively-optimized, personalized health maintenance plan for a user.

2. Description of the Related Art

As information and choices become more abundant, there is conversely a decrease in the amount of information individuals can assimilate. As a result, people avoid certain problems and issues when the amount of information needed to understand the problems and issues reaches a certain threshold. Yet, most people understand that information is power and solutions to problems and answers to issues can be found through the assimilation of information. Through existing information discovery and presentation systems, the possibility that better solutions and strategies exist for any individual greatly increases, but the odds of them finding those solutions and strategies either stays flat, or in fact diminishes.

People turn to experts to try and help them with their problems and issues as information and choices become more abundant, but unfortunately, the experts are often overloaded, lack up-to-date information, or are ambivalent regarding their client's needs. Or, perhaps the user cannot afford the price charged by such a professional consultant.

What is needed is an affordable and easy to use system that can collect, integrate, and present information and choices to individuals in a format that is controlled by the user and, therefore, is easy for the user to assimilate. Such a system is particularly valuable to the medical arts, where the average person wants to understand complex information pertaining to health, and particularly wants to understand personalized health information.

SUMMARY

The teachings generally related to a personalized information discovery and presentation system having an input device, a subject-profile module, an information database, an alignment module, a solutions module, an integration engine, a plan module, a graphical user interface, and a processor.

The teachings described herein are directed to a personalized health information discovery and presentation system for providing a health maintenance plan to a user. In some embodiments, the health maintenance plan comprises a care management plan, a disease management plan, or both.

In some embodiments, the system comprises an input device, a subject-profile module, an information database, an alignment module, a solutions module, an integration engine, a plan module, a graphical user interface, and a processor. The input device is operable to allow a user to enter a personalized subject-profile into the computing system, and the subject-profile module is operable to receive the personalized subject-profile and convert the subject-profile into a recognized health profile. The health information database comprises a library of health information, and the alignment module is operable to align the recognized health profile with relevant health information from the health information database. The solution's module is operable to parse the relevant information in the health information database into information subsets in response to the user selecting a customized set of information subset options, and the integration engine is operable to integrate the recognized health profile with the relevant health information; identify conflicting health information, contraindications, or health warnings obtained from the health information database; notify the user about the conflicting health information, contraindications, or health warnings obtained from the health information database; and compile data for presentation to the user, wherein the data is compiled using the customized set of information subset options. The plan module is operable to convert the integrated health information into a personalized health maintenance plan. The graphical user interface is operable to display the personalized health maintenance plan to the user.

In some embodiments, the subject-profile comprises one or more of the subject's age, sex, height, weight, known medical conditions, vital signs, laboratory test results, prior conditions, prior treatments, prescriptions, and family medical history. In some embodiments, the relevant health information includes the subject's activity, nutrition, stress, and sleep, and the solutions module is operable to parse the relevant health information into activity, nutrition, stress, and sleep. In these embodiments, the alignment engine is operable to align the library of health information with the subject's activity, nutrition, stress; and the plan module is operable to provide a personalized health maintenance plan consisting of the four categories of activity, nutrition, stress, and sleep.

The system can have the capability of optimizing information as it learns user preferences. In some embodiments, wherein the personalized health maintenance plan is a second personalized health maintenance plan optimized from a first personalized health maintenance plan by the user interactively answering additional queries generated by the system and derived at least in part from the subject-profile. In these embodiments, the second personalized health maintenance plan can be further optimized by the user interactively answering one or more additional queries generated by the system and derived at least in part on the subject-profile, wherein the personalized health maintenance plan is iteratively optimized at each level of questioning.

In some embodiments, the system comprises a data exchange module operable to interact with external medical data formats, wherein the subject-profile comprises external medical data obtained from a health provider's database. In some embodiments, the system further comprises a parameterization module operable to derive display-preference parameters from the user profile, and the graphical user interface displays the health maintenance plan in accordance with the user's display preferences and in the form of the customized set of information subset options.

In some embodiments, the system further comprising a multilanguage database, a translation engine, and a template look-up engine. The multilanguage database includes a plurality of phrase templates associated with a plurality of phrases in the recognized health profile and the library of health information, the translation engine is operable to translate the relevant phrase template from a source language to a destination language selected from multiple languages in the multilanguage database, and the template look-up engine is operable to find the phrase template associated with the destination phrase from among the multiple languages.

In some embodiments, the system further comprises an external computer connection and a browser program module. The browser program module is operable to access external data through the external computer connection to update the health information database.

In some embodiments, the system further comprises security measures to protect the subject's privacy, integrity of data, or both. In some embodiments, the system is provided by a network and, in some embodiments, the system is coupled to a network.

In some embodiments, the system is accessible through a portable, single unit device and, in some embodiments, the input device, the graphical user interface, or both, is provided through a portable, single unit device. In some embodiments, the portable, single unit device is a hand-held device.

In some embodiments, the plan module is further operable to select multimedia data forms to provide the user with the integrated health information through a layered hierarchy of multimedia. The layered hierarchy of multimedia can be provided in a manner selected by the user, wherein the layered hierarchy segments complex lessons into one or more lesson subsets in each layer of the layered hierarchy segments.

In some embodiments, the subject-profile includes data on the subject's personal interests, and the integration engine further functions enhance learning by (i) aligning the data on the subject's personal interests with relevant health information from the health information database; (ii) selecting relevant information in a manner that minimizes negative suggestion effect; and (iii) displaying the personalized health maintenance plan to the user in a manner that reflects the subject's personal interests.

In some embodiments, the integration engine further functions to enhance learning by (i) linking related information, (ii) removing unrelated information; and (iii) displaying the personalized health maintenance plan to the user in a manner that is focused to information and in accordance with the user's customized set of information subset options.

The present teachings also relate to a computer readable medium comprising a subject-profile module, a health information database, an alignment module, a solutions module, an integration engine, and a plan module. The input device is operable to allow a user to enter a personalized subject-profile into the computing system, and the subject-profile module is operable to receive the personalized subject-profile and convert the subject-profile into a recognized health profile. The health information database comprises a library of health information, and the alignment module is operable to align the recognized health profile with relevant health information from the health information database. The solution's module is operable to parse the relevant information in the health information database, where the information is parsed into information subsets in response to the user selecting a customized set of information subset options. The integration engine is operable to integrate the recognized health profile with the relevant health information; identify conflicting health information, contraindications, or health warnings obtained from the health information database; notify the user about the conflicting health information, contraindications, or health warnings obtained from the health information database; and present the information to the user in the in the form of the customized set of information subset options. The plan module is operable to convert the integrated health information into a personalized health maintenance plan. The subject-profile module, the health information database, the alignment module, the solutions module, the integration engine, and the plan module are components of a computer system and are coupled to a processor, an input device, and a graphical user interface; the graphical user interface being operable to display the personalized health maintenance plan to the user.

DETAILED DESCRIPTION OF THE INVENTION

Figure 1:
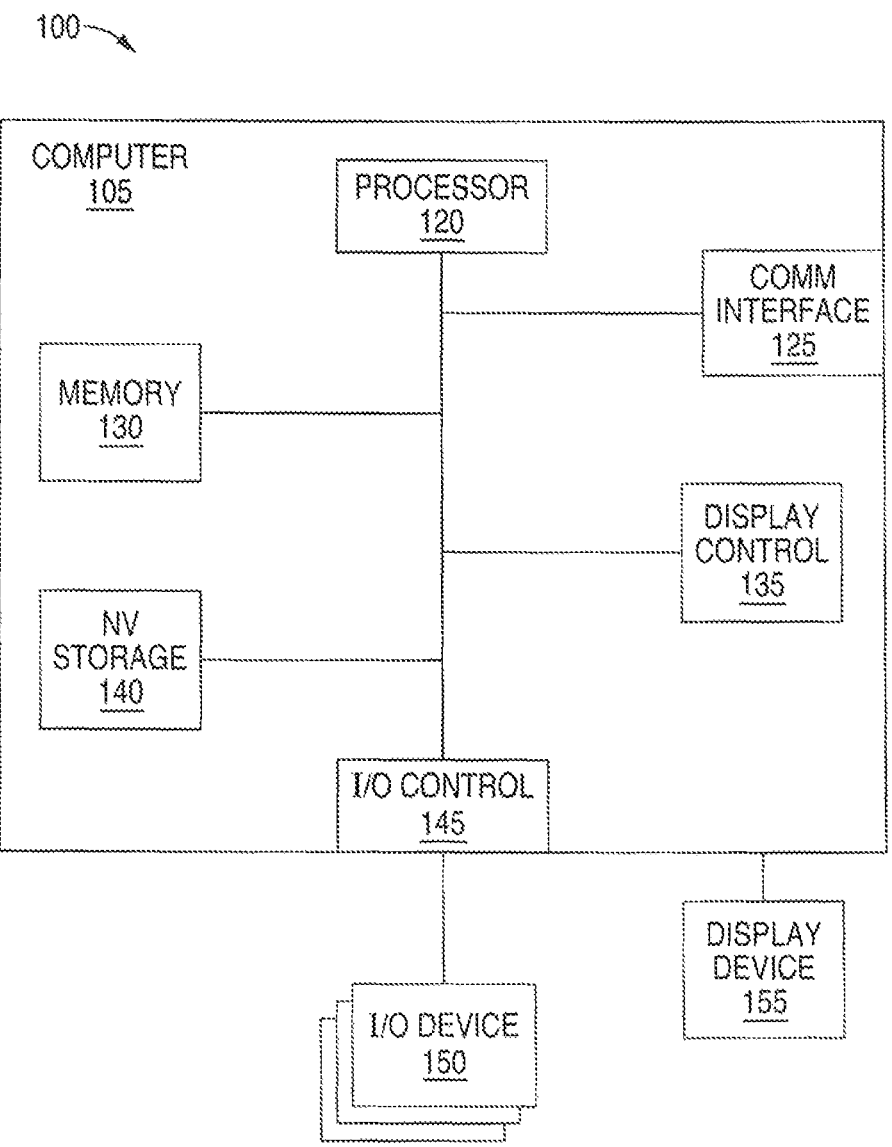
FIG. 1 shows a general technology platform for the information discovery and presentation system, according to some embodiments.

The teachings provided herein are generally directed to a personalized information discovery and presentation system, a system that can organize and present information and choices to individuals in an easy to use and customized format that informs as well as educates the individual. In addition to organizing the data, the system can also personalize the data by integrating data aligned with a personalized set of data provided by the user of the system. As such the information provided to the individual can be specialized or unique to that individual, as well as.

The teachings include a system for providing a personalized health maintenance plan that explicitly links and displays an integration and synthesis of complex health information. The system outlines and simplifies multiple layers of complex health information and associates the layers with personalized data entered by a user. The user can be the subject of the personalized data, or the user can be another individual producing the health maintenance plan for the subject. The health maintenance plan can be generated for use by the user, or by the subject. In some embodiments, the health maintenance plan comprises a care management plan, a disease management plan, or both. The system can be used, for example, by (i) health care providers, such as doctors, dentists, therapists, nutritionists, and the like; (ii) insurance providers; (iii) patients that are under the care of a health care provider; (iv) teachers; (v) athletic coaches; and (v) and other users that are otherwise interested in learning about health facts and how they interrelate and link between select subsets of such health facts.

In some embodiments, information about the user is gathered using templated questionnaires. A plan is presented to the user the information gathered. The plan can be shown in a visual flow chart, for example, having a layered hierarchy of information separated by subtopics and accessible by exploding sections of the visual flow chart. More information can collected on the user about the subtopics when the user accesses the sections of the visual flow chart. The plan can be optimized based on the collected information to produce an optimized plan that is specific to the user, and this optimized plan may be displayed as a second visual flow chart, the second visual flow chart having a different appearance than the first visual flow chart. In some embodiments, the flowcharts can be orbital flow charts.

In some embodiments, the system is interactive, in that the user provides feedback to further optimize the plan in an iterative fashion, such that a plan can be optimized, further optimized, and further optimized, until a desired plan is achieved. In some embodiments, the system is a learning system that performs iterations without user interaction, basing the iterations on past user inputs, answers, the subject-profile, and the like. In some embodiments, the user is prompted to optimize the plan due to relative quality of the data provided to the user, such that data can be identified as low quality or high quality depending on a statistical relationship between the subject-profile and the data obtained and parsed into desired categories.

In some embodiments, the information is parsed into sets of like information and the information can be shared between sets. For example, information collected in a particular section of a visual flow chart can also populate data in other sections of the visual flow chart. In some embodiments, the user is notified of updates to information, local activities and events, news, and other publications. In some embodiments, the user is asked to update the subject-profile and obtain updated personalized plans.

FIG. 1 shows a general technology platform for the information discovery and presentation system, according to some embodiments. The computer system 100 may be a conventional computer system and includes a computer 105, I/O devices 110, and a display device 115. The computer 105 can include a processor 120, a communications interface 125, memory 130, display controller 135, non-volatile storage 140, and I/O controller 145. The computer system 100 may be coupled to or include the I/O devices 150 and display device 155.

The computer 105 interfaces to external systems through the communications interface 125, which may include a modem or network interface. It will be appreciated that the communications interface 125 can be considered to be part of the computer system 100 or a part of the computer 105. The communications interface 125 can be an analog modem, isdn modem, cable modem, token ring interface, satellite transmission interface (e.g. "direct PC"), or other interfaces for coupling the computer system 100 to other computer systems. In a cellular telephone, this interface is typically a radio interface for communication with a cellular network and may also include some form of cabled interface for use with an immediately available personal computer. In a two-way pager, the communications interface 125 is typically a radio interface for communication with a data transmission network but may similarly include a cabled or cradled interface as well. In a personal digital assistant, the communications interface 125 typically includes a cradled or cabled interface and may also include some form of radio interface, such as a BLUETOOTH or 802.11 interface, or a cellular radio interface, for example.

The processor 120 may be, for example, a conventional microprocessor such as an Intel Pentium microprocessor or Motorola power PC microprocessor, a Texas Instruments digital signal processor, or a combination of such components. The memory 130 is coupled to the processor 120 by a bus. The memory 130 can be dynamic random access memory (DRAM) and can also include static ram (SRAM). The bus couples the processor 120 to the memory 130, also to the non-volatile storage 140, to the display controller 135, and to the I/O controller 145.

The I/O devices 150 can include a keyboard, disk drives, printers, a scanner, and other input and output devices, including a mouse or other pointing device. The display controller 136 may control in the conventional manner a display on the display device 155, which can be, for example, a cathode ray tube (CRT) or liquid crystal display (LCD). The display controller 135 and the I/O controller 145 can be implemented with conventional well known technology, meaning that they may be integrated together, for example.

The non-volatile storage 140 is often a FLASH memory or read-only memory, or some combination of the two. A magnetic hard disk, an optical disk, or another form of storage for large amounts of data may also be used in some embodiments, although the form factors for such devices typically preclude installation as a permanent component in some devices. Rather, a mass storage device on another computer is typically used in conjunction with the more limited storage of some devices. Some of this data is often written, by a direct memory access process, into memory 130 during execution of software in the computer 105. One of skill in the art will immediately recognize that the terms "machine-readable medium" or "computer-readable medium" includes any type of storage device that is accessible by the processor 120 and also encompasses a carrier wave that encodes a data signal. Objects, methods, inline caches, cache states and other object-oriented components may be stored in the non-volatile storage 140, or written into memory 130 during execution of, for example, an object-oriented software program.

The computer system 100 is one example of many possible different architectures. For example, personal computers based on an Intel microprocessor often have multiple buses, one of which can be an I/O bus for the peripherals and one that directly connects the processor 120 and the memory 130 (often referred to as a memory bus). The buses are connected together through bridge components that perform any necessary translation due to differing bus protocols.

In addition, the computer system 100 is controlled by operating system software which includes a file management system, such as a disk operating system, which is part of the operating system software. One example of an operating system software with its associated file management system software is the family of operating systems known as Windows CE® and Windows® from Microsoft Corporation of Redmond, Wash., and their associated file management systems. Another example of operating system software with its associated file management system software is the LINUX operating system and its associated file management system. Another example of an operating system software with its associated file management system software is the PALM operating system and its associated file management system. The file management system is typically stored in the non-volatile storage 140 and causes the processor 120 to execute the various acts required by the operating system to input and output data and to store data in memory, including storing files on the non-volatile storage 140. Other operating systems may be provided by makers of devices, and those operating systems typically will have device-specific features which are not part of similar operating systems on similar devices. Similarly, WinCE® or PALM operating systems may be adapted to specific devices for specific device capabilities.

The computer system 100 may be integrated onto a single chip or set of chips in some embodiments, and typically is fitted into a small form factor for use as a personal device. Thus, it is not uncommon for a processor, bus, onboard memory, and display/I-O controllers to all be integrated onto a single chip. Alternatively, functions may be split into several chips with point-to-point interconnection, causing the bus to be logically apparent but not physically obvious from inspection of either the actual device or related schematics.

Figure 2:
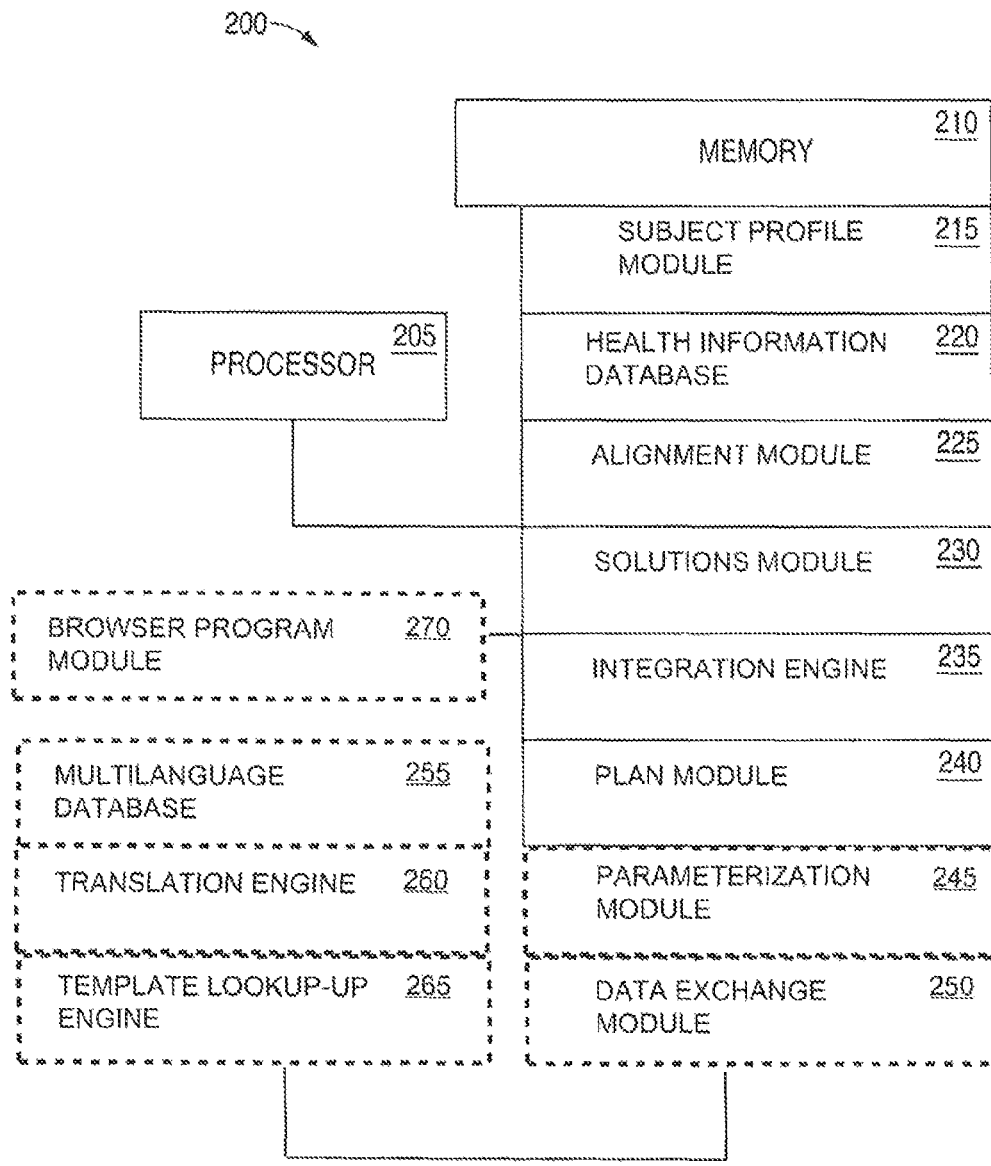
FIG. 2 illustrates a processor-memory diagram to describe components of the personalized health information discovery and presentation system according to some embodiments.

FIG. 2 illustrates a processor-memory diagram to describe components of the personalized health information discovery and presentation system according to some embodiments. The system 200 shown in FIG. 2 contains a processor 205 and a memory 210 (that can include non-volatile memory), wherein the memory 210 includes a subject-profile module 215, a health information database 220, an alignment module 225, a solutions module 230, an integration engine 235, and a plan module 240.

The system includes an input device (not shown) operable to allow a user to enter a personalized subject-profile into the computing system. Examples of input devices include a keyboard, a mouse, a data exchange module operable to interact with external data formats, voice-recognition software, a hand-held device in communication with the system, and the like.

The subject-profile module 215 is operable to receive the personalized subject-profile and convert the subject-profile into a recognized health profile. In some embodiments, the system can provide a set of data entry forms, surveys, screens and tools from which the system can receive information from users. In some embodiments, the system can access any of a variety of accessible data through a data exchange module, as discussed above. The health information database 220 comprises a library of health information, and the alignment module 225 is operable to align the recognized health profile with relevant health information from the health information database 220.

In some embodiments, the subject-profile comprises one or more of the subject's age, sex, height, weight, known medical conditions, vital signs, laboratory test results, prior conditions, prior treatments, prescriptions, and family medical history. In some embodiments, the relevant health information includes the subject's activity, nutrition, stress, and sleep, and the solutions module is operable to parse the relevant health information into activity, nutrition, stress, and sleep. In these embodiments, the alignment module is operable to align the library of health information with the subject's activity, nutrition, stress; and the plan module 240 is operable to provide a personalized health maintenance plan consisting of the four categories of activity, nutrition, stress, and sleep. consisting of the four categories of activity, nutrition, stress, and sleep.

The system can have the capability of optimizing information as it learns user preferences. In some embodiments, wherein the personalized health maintenance plan is second personalized health maintenance plan optimized from a first personalized health maintenance plan by the user interactively answering additional queries generated by the system and derived at least in part from the subject-profile. In these embodiments, the second personalized health maintenance plan can be further optimized by the user interactively answering one or more additional queries generated by the system and the subject-profile, wherein the personalized health maintenance plan is iteratively optimized at each level of questioning.

In some embodiments, the subject-profile comprises one or more of the subject's age, sex, height, weight, known medical conditions, vital signs, laboratory test results, prior conditions, prior treatments, prescriptions, and family medical history. In some embodiments, the relevant health information includes the subject's activity, nutrition, stress, and sleep, and the solutions module is operable to parse the relevant health information into activity, nutrition, stress, and sleep. In these embodiments, the alignment engine is operable to align the library of health information with the subject's activity, nutrition, stress; and the plan module 240 is operable to provide a personalized health maintenance plan consisting of the four categories of activity, nutrition, stress, and sleep.

The subject-profile can include any of a variety of personal information that is valuable to linking information to an individual, including activities, health problems, health history and family history. Some responses may lead to further questionnaires, for example, if a person is diabetic they may be further asked how often are they receiving injections. The subject-profile can be update and, in some embodiments, this occurs interactively. As users browse through the exploded sub topics, and sub-sub-topics, they are prompted for more answers on the particular sub-topics. In this manner, questions are spread out as to not overwhelm the user. Linking questions within sub-topics may be asked to better understand answers provided by the user. For example, the user might be asked what their blood pressure is, but learns from the information that they shouldn't measure this first thing in the morning. Or they might be asked how many whole grains they are eating, and learns that multi-grains are not the same things as whole grains. Answering question in one subtopic area may also alter the questions populated in the other areas, and may also create new sub topics off of the plan. Essentially, the plan is optimized by relating broad topics and sub-topics to the subject-profile to limit the amount of information obtained. The system can also cross reference information across subtopics, so that interactions between the subtopics is processed specific to the individual. In the example given above, a diabetic with high blood pressure will have concerns unique to that condition. The engine at this point may also pull in relevant subtopics that the user was not aware were relevant, such as a prompt that the user may be at a high risk for a vascular disease that they were thus far unaware.

The solution's module 230 is operable to parse the relevant information in the health information database 220 into information subsets in response to the user selecting a customized set of information subset options. And, the integration engine 235 is operable to integrate the recognized health profile with the relevant health information; identify conflicting health information, contraindications, or health warnings obtained from the health information database 220; notify the user about the conflicting health information, contraindications, or health warnings obtained from the health information database 220; and compile data for presentation to the user, wherein the data is compiled using the customized set of information subset options. The plan module 240 is operable to convert the integrated health information into a personalized health maintenance plan. The graphical user interface (not shown) is operable to display the personalized health maintenance plan to the user.

In some embodiments, the subject-profile includes data on the subject's personal interests, and the integration engine 235 further functions enhance learning by (i) aligning the data on the subject's personal interests with relevant health information from the health information database 220; (ii) selecting relevant information in a manner that minimizes negative suggestion effect; and (iii) displaying the personalized health maintenance plan to the user in a manner that reflects the subject's personal interests. In some embodiments, the integration engine 235 further functions to enhance learning by (i) linking related information, (ii) removing unrelated information; and (iii) displaying the personalized health maintenance plan to the user in a manner that is focused to information and in accordance with the user's customized set of information subset options.

In some embodiments, the plan module 240 is further operable to select multimedia data forms to provide the user with the integrated health information through a layered hierarchy of multimedia. The term "multimedia" is used in contrast to media which only utilize traditional forms of printed or hand-produced text and still graphics. In general, multimedia includes any combination of text, audio, still images, animation, video, and interactivity content forms. The layered hierarchy of multimedia can be provided in a manner selected by the user, wherein the layered hierarchy segments complex lessons into one or more lesson subsets in each layer of the layered hierarchy segments.

The system can have additional functions. In some embodiments, the system further comprises a parameterization module operable 245 to derive display-preference parameters from the user profile, and the graphical user interface displays the health maintenance plan in accordance with the user's display preferences and in the form of the customized set of information subset options. For example, the user may prefer a select combination of shapes, colors, sound, and any other of a variety of screen displays and multimedia options. Furthermore, the user can personalize and change the display-preference parameters easily and at any time In some embodiments, the system further comprises a data exchange module 250 operable to interact with external medical data formats, wherein the subject-profile comprises external medical data obtained from a health provider's database. In some embodiments, the data exchange module includes an ePHR data exchange module. This module allows the system to interact with external ePHR/EMRs using standard medical data formats such as Continuity of Care Record (CCR) and Continuity of Care Document (CCD) data. In addition, the system will allow data exchange using a proprietary SOAP based API enabling integration with future technologies based on the SOAP/XML protocols.

In some embodiments, the system further comprises a multilanguage database 255, a translation engine 260, and a template look-up engine 265. The multilanguage database 255 includes a plurality of phrase templates associated with a plurality of phrases in the recognized health profile and the library of health information, the translation engine 260 is operable to translate the relevant phrase template from a source language to a destination language selected from multiple languages in the multilanguage database 255, and the template look-up engine 265 is operable to find the phrase template associated with the destination phrase from among the multiple languages.

In some embodiments, the system further comprises a messaging module (not shown) operable to allow users to communicate with other users having like subject-profiles, or others users in a profile independent manner, merely upon election of the user. The users can email one another, post blogs, or have instant messaging capability for real-time communications. In some embodiments, the users have video and audio capability in the communications, wherein the system implements data streaming methods known to those of skill in the art.

The systems taught herein can be practiced with a variety of system configurations, including personal computers, multiprocessor systems, microprocessor-based or programmable consumer electronics, network PCs, minicomputers, mainframe computers, and the like. The invention can also be practiced in distributed computing environments where tasks are performed by remote processing devices that are linked through a communications network. As such, in some embodiments, the system further comprises an external computer connection and a browser program module 270. The browser program module 270 is operable to access external data through the external computer connection to update the health information database 220.

Figure 3:
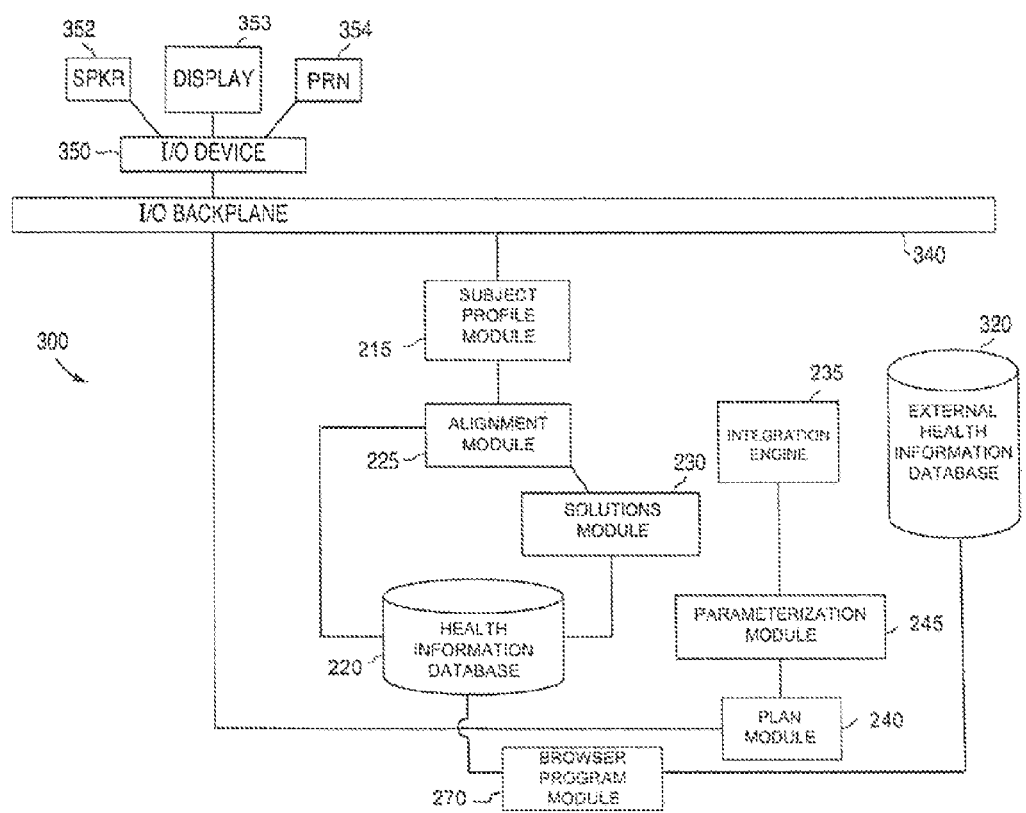
FIG. 3 is a concept diagram illustrating the personalized health information discovery and presentation system according to some embodiments.

FIG. 3 is a concept diagram illustrating the personalized health information discovery and presentation system according to some embodiments. The system 300 contains components that can be used in a typical embodiment. In addition to the subject-profile module 215, health information database 220, the alignment module 225, the solutions module 230, the integration engine 235, and the plan module 240 shown in FIG. 2, the memory 210 of the device 300 also includes parameterization module 245 and the browser program module 270 for accessing the external health information database 320. The system includes a speaker 352, display 353, and a printer 354 connected directly or through I/O device 350 connected to I/O backplane 340.

The system can be implemented in a stand-alone device, rather than a computer system or network. In FIG. 3, for example, the I/O device 350 connects to the speaker (spkr) 352, display 353, and microphone (mic) 354, but could also be coupled to other features. In a device offering language translation, the device can have a source language state selector and a destination language state selector connected directly to the I/O backplane 340. In many embodiments, the system can also a mute/volume state selector connected directly to the I/O backplane 340. Other features can be added such as, for example, an on/off button, a start button, an ear phone input, and the like. In some embodiments, the system can turn on and off through motion. In some embodiments, the system can have a state selector to select a preprogrammed voice that is pleasing to the user, such as a voice that would make a child think of a bear, a kitten, a monkey, a puppy, a mouse, and the like.

Figure 4:
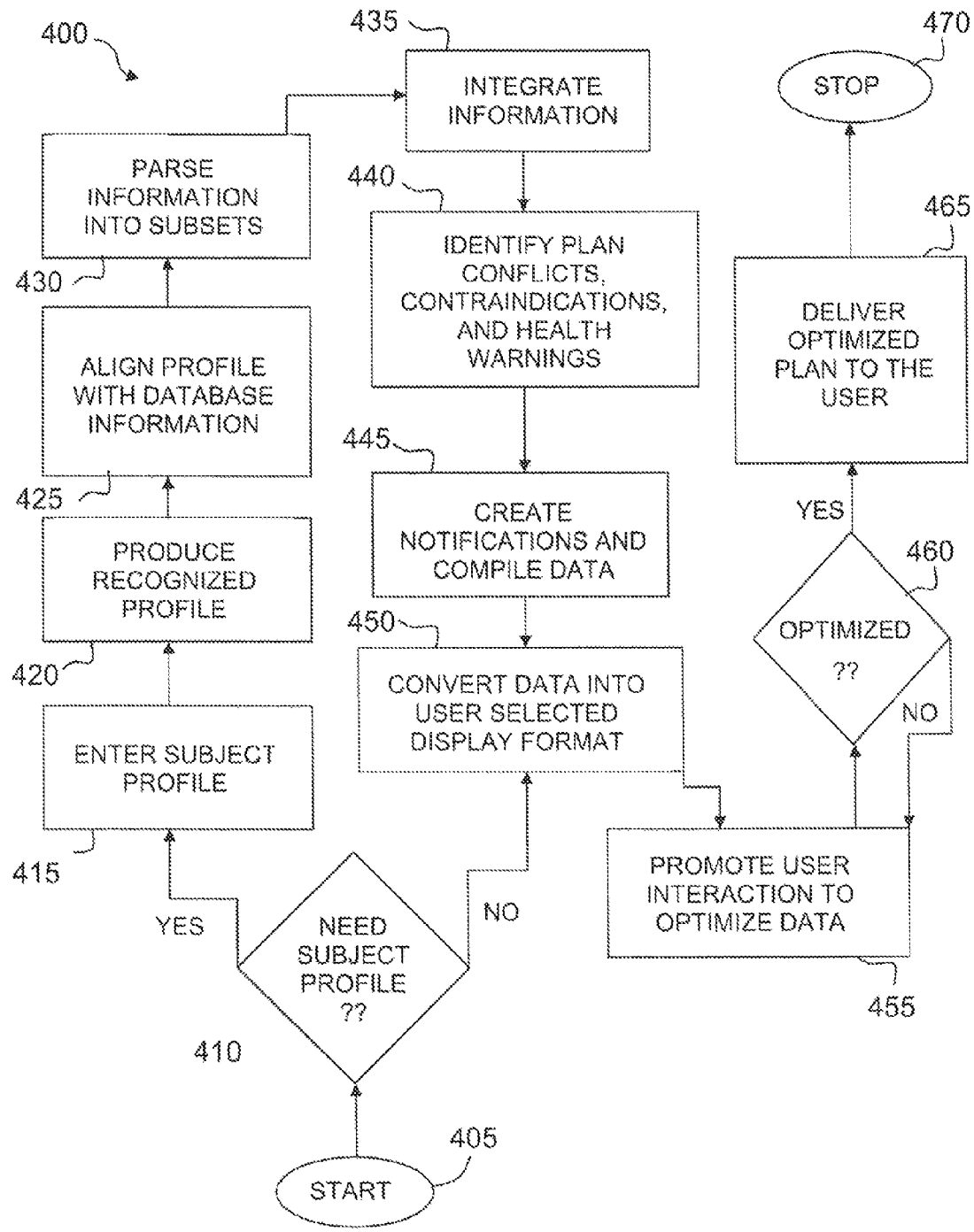
FIG. 4 is a diagram of the logic of the system for the personalized health information discovery and presentation system according to some embodiments.

FIG. 4 is a diagram of the logic of the system for the personalized health information discovery and presentation system according to some embodiments. In such embodiments, the system will start 405 teaching by determining whether the system needs a subject-profile for that task. If the answer is no, the system has recognized that the required subject-profile has been entered and will access and convert data into the user selected display format. Of course, the user can have the opportunity to re-enter and/or update the information. In some embodiments, the updates include electronically accessed information from health care providers. If the answer is yes, the system will prompt the user to enter 415 a personalized, subject profile. The system will then produce 420 a recognized health profile using the subject-profile module and align 425 the recognized health profile with the health information database information using the alignment module. The system will then parse 430 the information into subsets using the solutions module, and integrate 435 the information using the integration engine. The integration engine will identify 440 plan conflicts, contraindications, and health warnings, create 445 notifications about the conflicts, contraindications, and health warnings, and compile data. The system then converts 450 the data into the user selected display format using the plan module.

A plan conflict can arise, for example, where a user receives conflicting information in response to a subject-profile. In some embodiments, the system accesses information from the health information database, which can access the information entirely within the existing database or from external sources, and such information can be conflicting. In these embodiments, for example, the subject may be recommended to increase activity from one information source, whereas another source may recommend a decrease in activity.

A contraindication can arise, for example, where a condition which makes a particular treatment or procedure inadvisable. In some embodiments, one condition may call for the administration of one or more types of drugs. A contraindication may arise where another condition prohibits the use of one or more of those drugs. Contraindications may be absolute or relative. An absolute contraindication is a situation which makes a particular treatment or procedure absolutely inadvisable. In a baby, for example, aspirin may be absolutely contraindicated because of the danger that aspirin will cause Reye syndrome. A relative contraindication is a condition which makes a particular treatment or procedure somewhat inadvisable but does not rule it out. For example, X-rays in pregnancy are relatively contraindicated because of concern for the developing fetus, unless the X-rays are absolutely necessary.

A health warning can arise, for example, where the system makes reference to an official declaration that a particular substance or activity in the subject-profile is dangerous, and can also arise where information otherwise relevant to the subject-profile is obtained, where that information is considered sufficiently relevant to justify the health warning. Information becomes sufficiently relevant where the general health community would feel that it is reasonable to advise the subject to consult with a health professional. The law now requires, for example, that the surgeon general health warnings be placed on every package of cigarettes. One of skill will appreciate that conflicts, contraindications, and health warnings can arise in a multitude of circumstances that are much too numerous to list in this teachings and, thus, much too numerous for any one health professional to amass as part of a single professional practice. Thus, such information represents information that would be highly desired by the user of the systems taught herein.

Figure 5A:
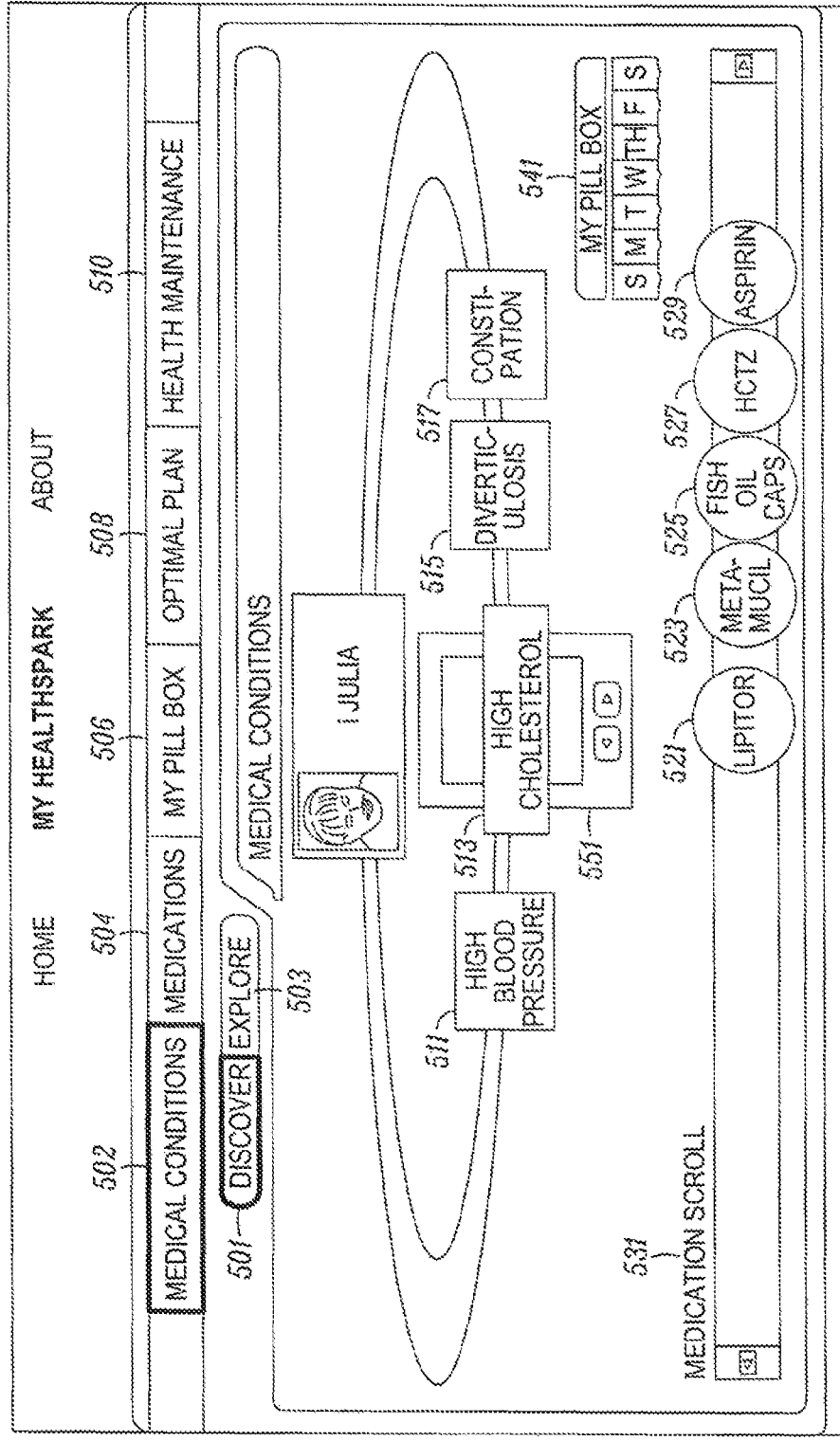
FIGS. 5A and 5B illustrate the discovery and exploration functions of the system for the personalized health information discovery and presentation system according to some embodiments.
Figure 5B:
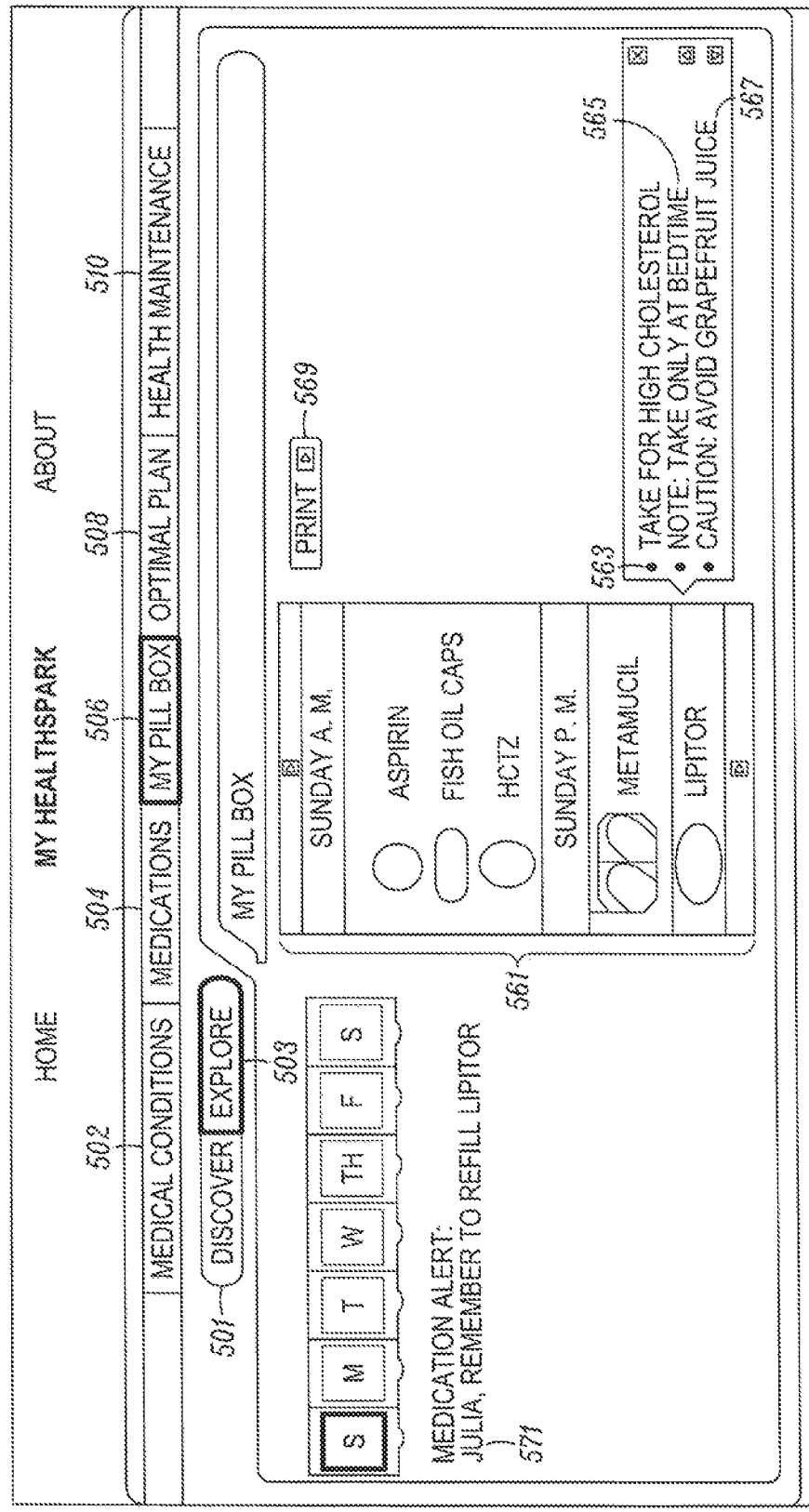

FIGS. 5A and 5B illustrate the discovery and exploration functions of the system for the personalized health information discovery and presentation system according to some embodiments. FIGS. 5A and 5B show how a user can use the parts 500 of the system to discover 501 and explore 503 information derived from the health database and the subject-profile. As described herein, the system uses a hierarchy of layers to control the complexity and presentation of information that may otherwise be too insurmountable and complex in quantity and arrangement to assimilate. In FIG. 5A, the user has five primary selections to discover and explore: Medical Conditions 502, Medications 504, My Pill Box 506, Optimal Plan 508, and Health Maintenance 510. In this instance, the user has selected Medical Conditions 502 as the primary selection from this layer of the information hierarchy. This selection provided a list of conditions from the subject-profile, such as high blood pressure 511, high cholesterol 513, diverticulosis 515, and constipation 517. The user then decided to discover more about a particular condition, so the user selected Discover 501 to show, for example, the medications 521-529 (LIPITOR, METAMUCIL, fish oil capsules, HCTZ, aspirin, respectively) listed in the subject-profile, as well as the relationship between the medications and the conditions.

In FIG. 5A, for example, the system cross-referenced the use of LIPITOR 521 with the condition of high cholesterol 513, linking the drug to the condition. In some embodiments, the user has the option of using the Medication Scroll 531 function to cross-reference by medication or, as shown in FIG. 5A, cross-reference by the Medical Conditions 502. In some embodiments, the primary selection and reference selection can be switched by first selecting Medications 504 as the primary screen, and then cross-referencing to condition. In some embodiments, the user can continue to drill-down the information hierarchy to gain more and more information on each of the primary and reference selections, thus gaining control of the amount and level of complexity of the information provided. For example, in FIG. 5A, the user can also choose the My Pill Box 541 sub-reference selection, for example, to immediately see the prescription plan provided in the subject-profile. As such, the user has a powerful information assimilation tool. This powerful tool is able to teach the user a complex set of information by integrating information that may be otherwise in an insurmountable quantity. The information is presented as a hierarchy of information that reduces the complexity of the information and links the information in useful sub-parts. In some embodiments, the user is able to design and control the amount, complexity, and format of information presented, as well as choose presentation display options to control, for example, the shapes, colors, speed of motion, sound, video 551, and the like of the multimedia available through the system and its health information database to stimulate the learning process.

In some embodiments, other primary selections include My Pill Box 506, Optimal Plan 508, and Health Maintenance 510. In many embodiments, each of the primary selections has a hierarchy of sublevels, each of which may or may not be shared with other of the primary selections. This is because each sublevel can have a function that is particular to the particular primary selection.

In FIG. 5B, the user has selected My Pill Box 506 as the primary selection and has decided to explore 503 the prescription plan provided in the subject-profile. The system responds by providing a graphical display corresponding to a day selected by the user that is easy for the user to understand, for example, a picture/text/date display 561 relating a visual of a pill with a name of the pill and scrollable to peruse dates of interest.

The system also provides important Medication Alerts 571 that include, for example, reminders to refill prescriptions. As described in 5A, the user can have the ability to continue to drill-down for information of higher complexity and more substantial content regarding the items shown. As shown in FIG. 5B, however, the system did not wait for a user selection to provide a layer of information describing the uses 563 of a particular medication, an important note 565 where advisable, and an example of a caution 567, which may be considered a health warning or a relative contraindication. In this embodiment, the system is designed to automatically and immediately provide this type of desired information to inform the user. In some embodiments, select layers can be labeled as urgent information, and the types of information with such urgency can be selected by the user, an administrator, and the like to provide additional control over the information presented. Each layer of the information hierarchy can be printed using a print selection 569, in most embodiments, to enable to the user to keep hardcopy records of the learning experience. In some embodiments, the user can request that the system check for conflicts, contraindications, and health warnings using the default collection settings, which filters the information according level of relevance, or the user can further open or further limit what the system considers to be relevant to the user. For example, the user may choose to check for drug interactions using a Drug Interaction selection available as a sub-selection, in some embodiments. In these embodiments, the user may have the flexibility to select the level of information filtration to collect more or less information from the system regarding possible and suspected drug interactions.

Figure 6A:
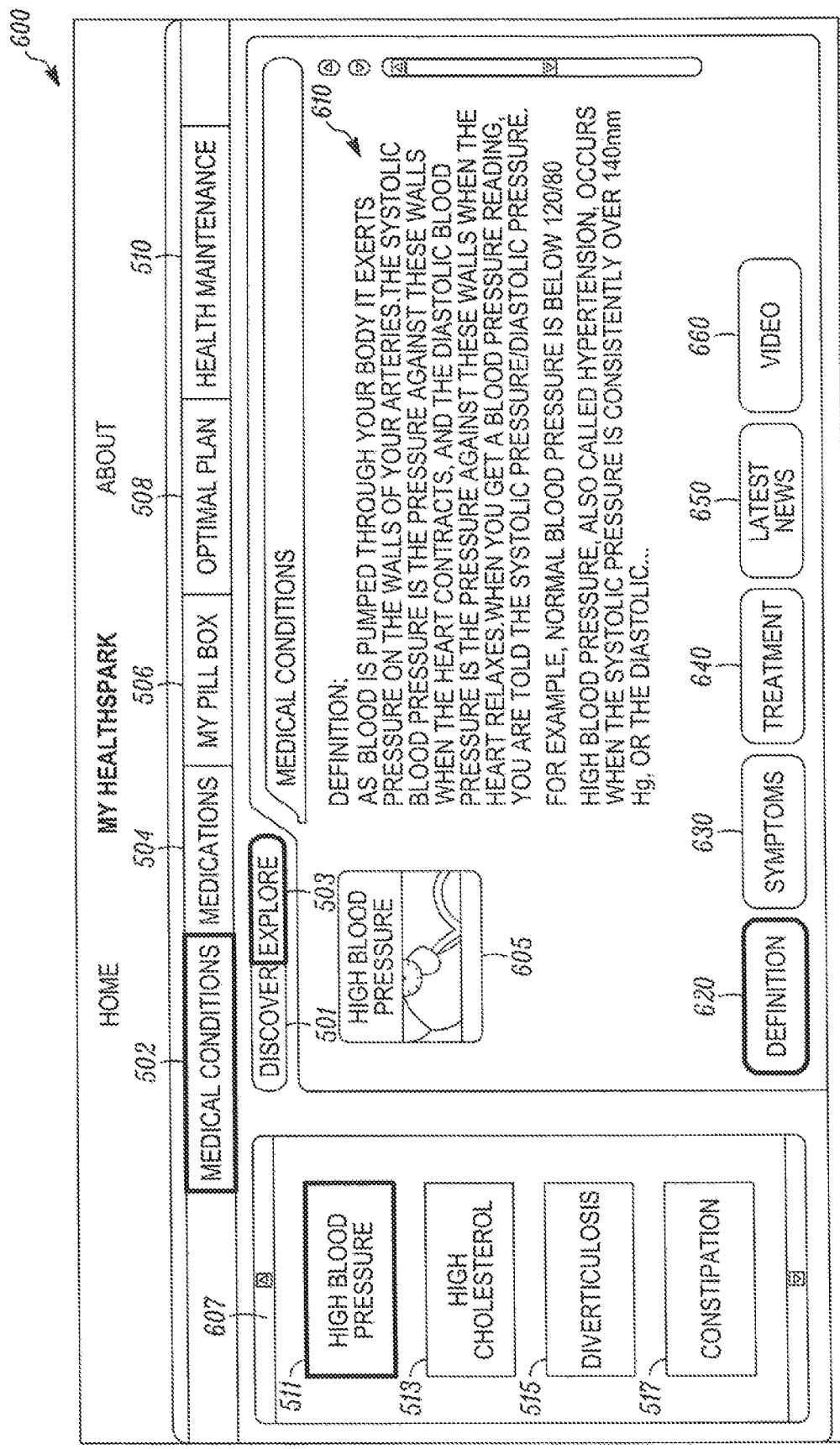
FIGS. 6A and 6B illustrate how the user can drill-down into the personalized health information discovery and presentation system to obtain more information about the conditions and medications at additional levels in the hierarchy according to some embodiments.
Figure 6B:
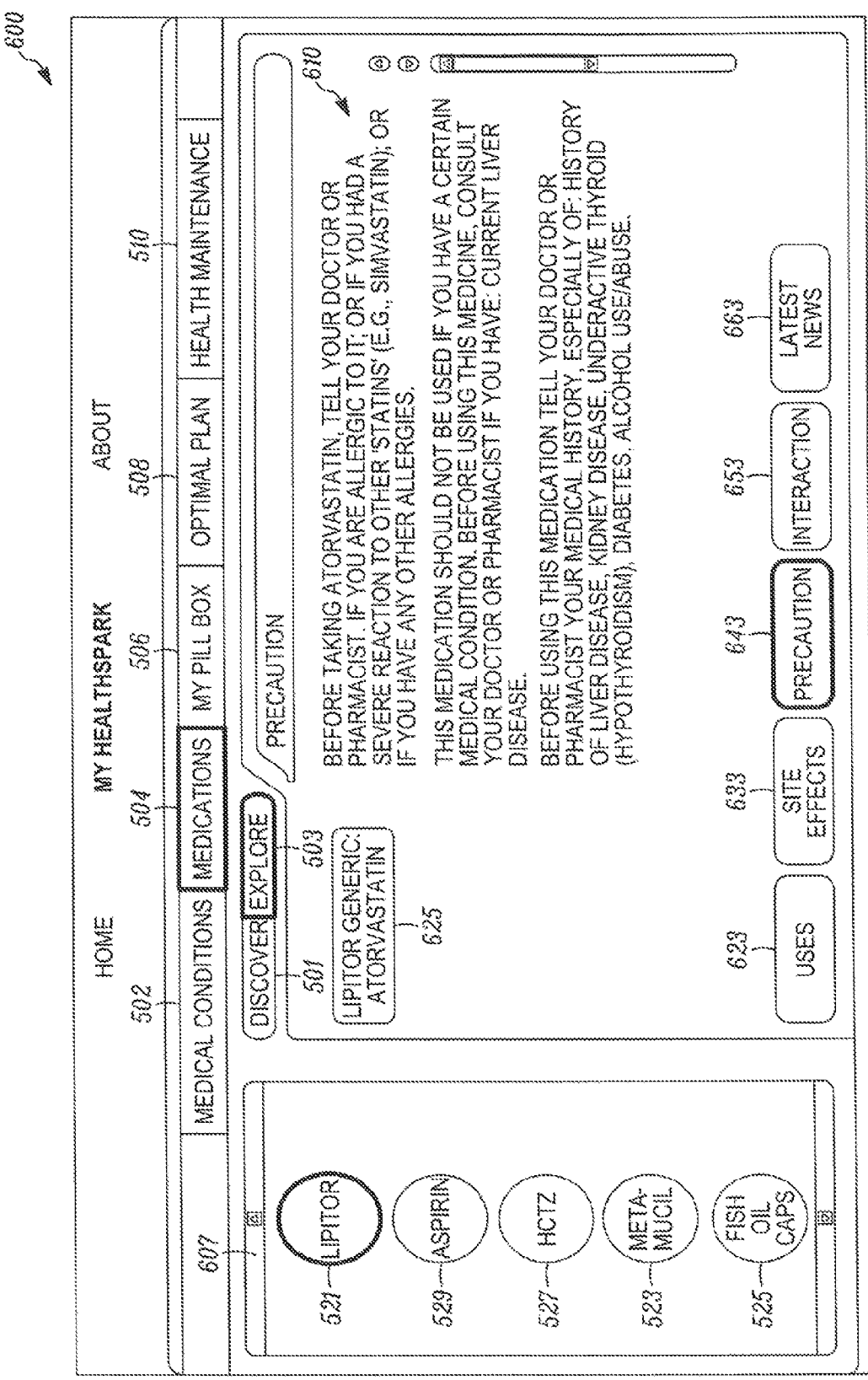

FIGS. 6A and 6B illustrate how the user can drill-down into the personalized health information discovery and presentation system to obtain more information about the conditions and medications at additional levels in the hierarchy according to some embodiments. In some embodiments the user first selects a primary selection and then a function. In FIG. 6A, for example, the user selected Medical Conditions 502 and Explore 503. The user then goes to the primary selection scrollable drop-down screen 607 to enable selection of a condition, in the event Medical Conditions are chosen as the primary selection. In some embodiments, the drop-down screen 607 can contain only the primary selection options, only the secondary (cross-reference) selection options, or it can be either the primary and secondary selection options, depending on the user and/or administrator preferences. Note that, in some embodiments, the user can select any of a range of information subset options. For example, in FIG. 6A, the primary selection of Medical Conditions 502 is in the drop-down screen 607, and the user has the ability to select from Definitions 620, Symptoms 630, Treatment 640, Latest News 650, and Videos 660. This hierarchy layering and multitude provides the user with control over the layer of information presented from the information hierarchy, as well as control over the multimedia used to present the information.

In FIG. 6A, the user selected high blood pressure 511 and Definitions 620 to obtain a definition for a condition provided by the subject-profile. An image appears to relate the condition to a visual display 605, which serves to link a visual learning tool with the definition. The definition appears in a scrollable text display 610. The user can read the definition and decide to further learning by investigating additional information that has been parsed into Symptoms 630, Treatment 640, Latest News 650, and Videos 660, to further reinforce learning using any of a variety of multimedia forms of display.

In FIG. 6B, the user wanted to learn more about the medications and selected Medications 504 from the primary selection menu and the function Explore 503. The drop-down menu provided the list of medications 521-529 provided by the subject-profile. In this embodiment, the user can select from a set of information subset options that include Uses 623, Side Effects 633, Precaution 643, Interaction 65, and Latest News 663, for example. The user selected Precaution 643, and the scrollable text display 610 provided a text explanation of precautions associated with LIPITOR 521, also highlighted in the medication display 625.

Figure 7A:
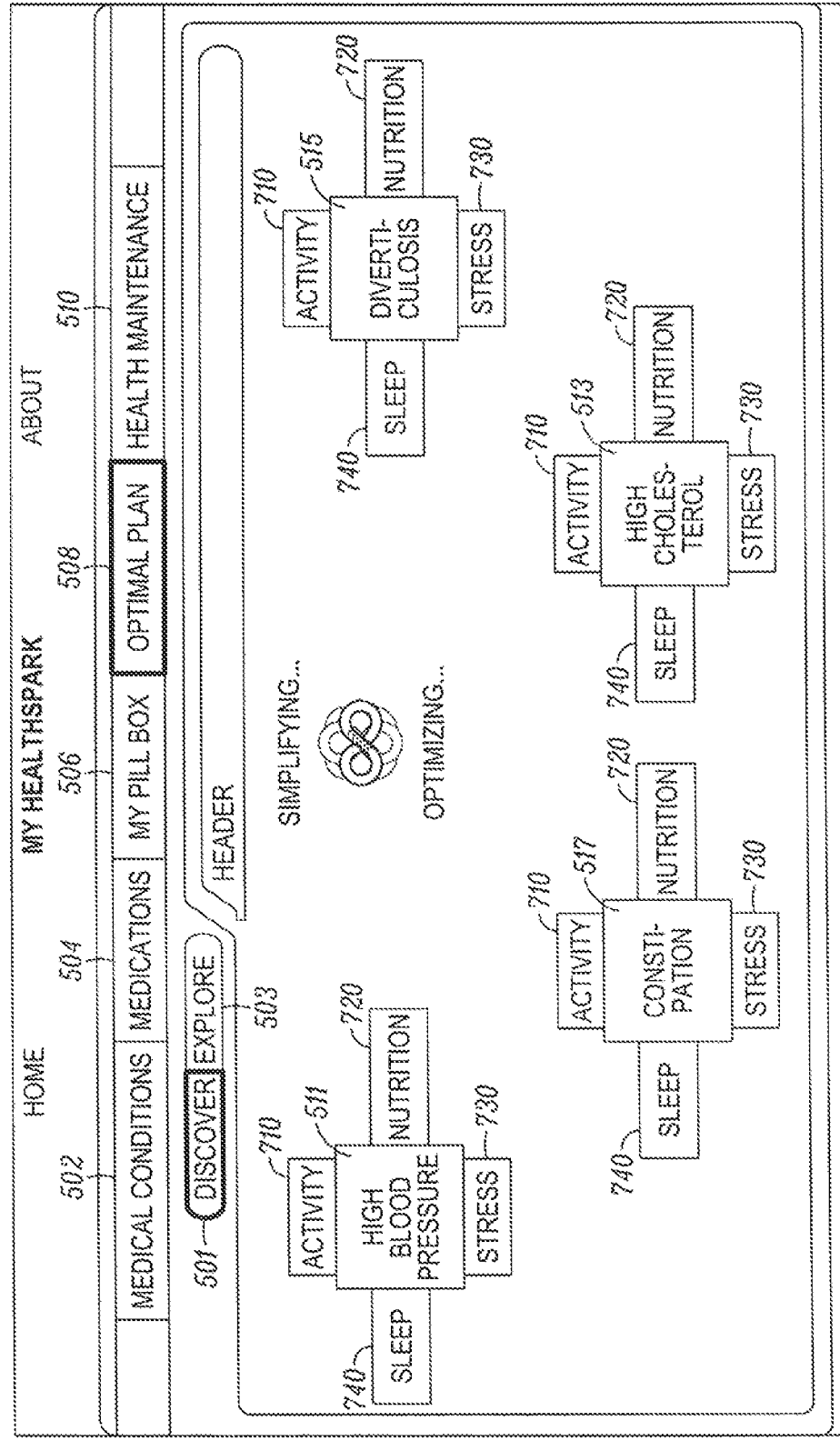
FIGS. 7A and 7B illustrate how the system can parse information into subject areas using the system for the personalized health information discovery and presentation system according to some embodiments.
Figure 7B:
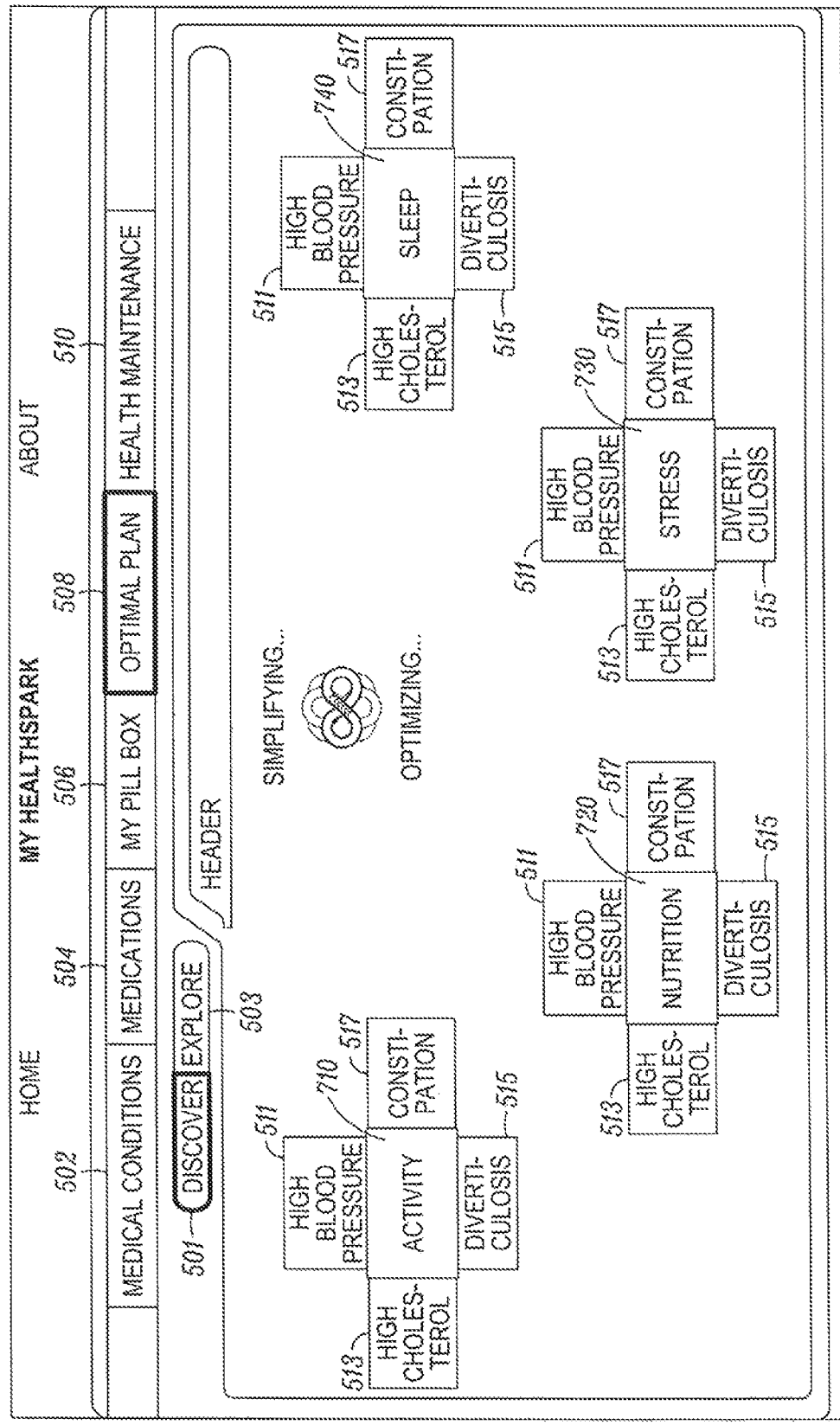

FIGS. 7A and 7B illustrate how the system can parse information into subject areas using the system for the personalized health information discovery and presentation system according to some embodiments. The user, for example, may want to develop a personalized health maintenance plan. In some embodiments, the plan can be parsed into categories using default settings of the system and, in some embodiments, the user can control the categories in which the information is parsed in order to personalize the presentation of information. In FIG. 7A, the user selected the Optimal Plan 508 primary selection and Discover 501 to visualize the structure of the subject's personalize plan. The user first organized the information by conditions 511-517 listed in the subject-profile, whereby the information is linked into desired subsets of information for each condition. In this example, the user elected to parse the information into desired subsets of activity 710, nutrition 720, stress 730, and sleep 740. One of skill will appreciate that these particular subsets are accepted in the art as main categories in which to parse health information and health concerns. In fact, in some embodiments, the system has a default setting that includes information parsing into these 4 subsets of information for layering, providing a well-organized and relevant layering of information for ease of learning and comprehension. In FIG. 7B, the user elected to display the information by the 4 categories first, and then link each category to the conditions listed in the subject-profile. The user can drill-down into each of the elements 511-517,710-740 in each of the displays in FIGS. 7A and 7B to uncover additional layers of information by merely clicking on the screen.

It should be appreciated that any of the drill-downs for information at any point in the use of the system functions can be performed using any method known to one of skill. For example, such methods include clicking on the screen using a mouse, clicking on menu options using a mouse, using shortcut keys with a keyboard or keypad, using a stylus or touchpad, or using voice commands or motion sensory commands.

Figure 8A:
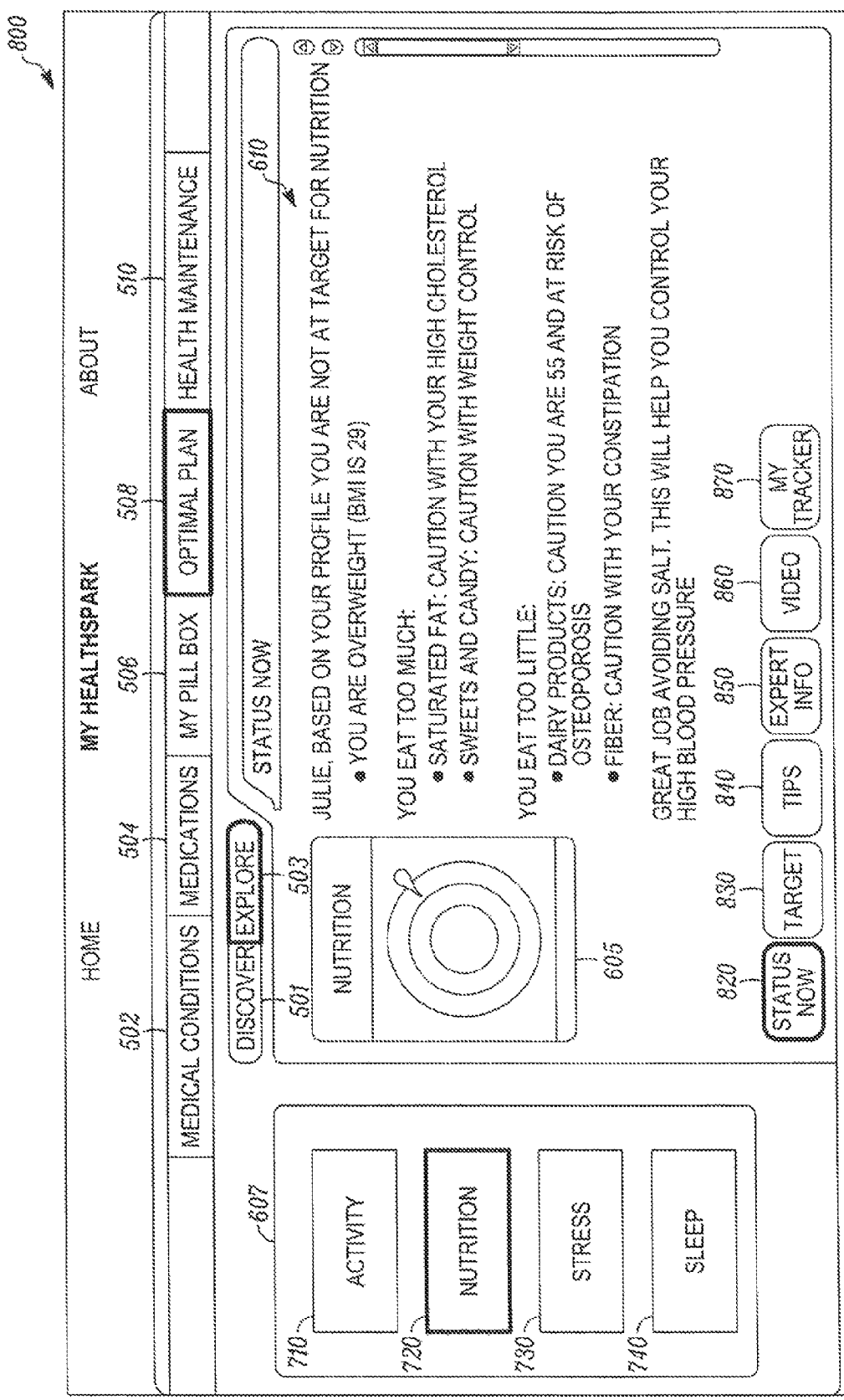
FIGS. 8A and 8B illustrate how the user can drill-down into the personalized health information discovery and presentation system to obtain more information about the plan at additional levels in the hierarchy according to some embodiments.
Figure 8B:
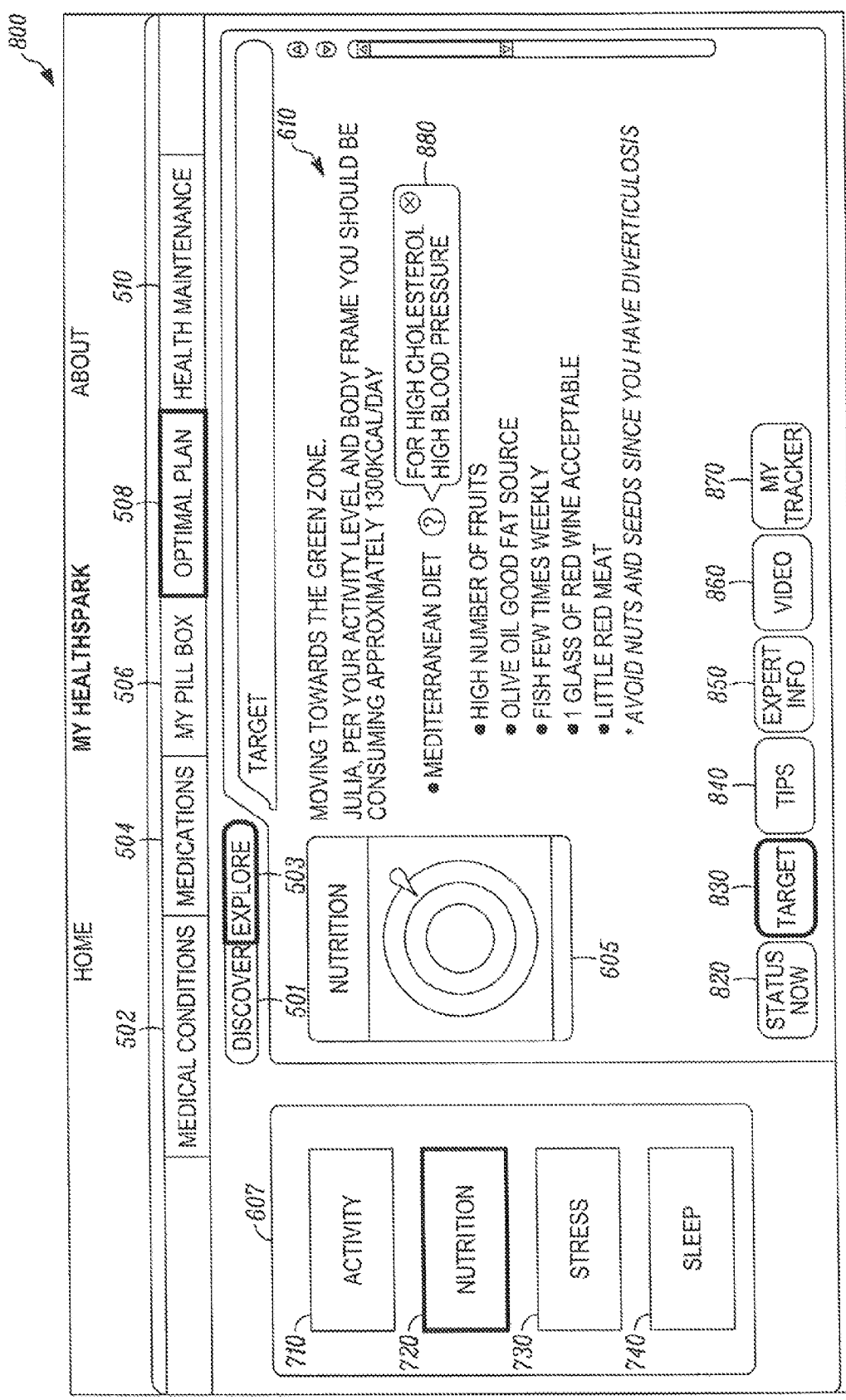

FIGS. 8A and 8B illustrate how the user can drill-down into the personalized health information discovery and presentation system to obtain more information about the plan at additional levels in the hierarchy according to some embodiments. The user, for example, may want to learn more about the subject's status in view of the subject-profile. In FIG. 8A, the user selected Optimal Plan 508 as the primary menu selection and the function Explore 503 to obtain a drop-down screen 607 showing the four desired information categories 710-740. The user then selected Nutrition 720 from the drop-down screen 607, and this selection appeared in visual display 605. The user can then select a next layer of information in the Optimal Plan 508 hierarchy of information, wherein the next layer is selected from the subset selections shown, including Status Now 820, Target 830, Tips 840, Expert Info 850, Video 860, and My Tracker 870. In some embodiments, the system provides default definitions for parsing information into such categories and, in some embodiments, the definitions are selected by the user, administrator, or both. Regardless, the categories and respective parsing definitions have been chosen for their relevance to the category selected from the drop-down screen 607.

In FIG. 8A, the user was interested in knowing the current health status of the subject and selected Status Now 820. Scrollable text display 610 provide the user with information about the subject. In this example, the user is the subject and is directed about her nutrition status, such as she's not on target for nutrition, is overweight, eats too much saturated fat and sweets, eats too little dairy products and fiber, and is doing a good job on salt intake. In some embodiments, each status report can provide cautions to consider and further explanations. The visual display also provides a graphical indication of the subject's status, where the display provides an indication of the subject's status with regard to target goals in that category.

In FIG. 8B, the user was interested in learning more about the target goals for the category of Nutrition 720. The user selected Target 830 and the scrollable text display 610 provided information in that layer of the information hierarchy for Nutrition 720. In this example, the information again included a brief excerpt about status, but discussed Nutrition in terms of target activities. The information went on to discuss calorie requirements, diet considerations and recommendations, and added cautions to ensure that the user is aware of foods that can affect her other conditions listed in the subject-profile. Added information pops up as added prompt 880 which, in this example, is explaining the benefits of a Mediterranean diet, as such a diet relates to the conditions listed in the subject-profile.

In some embodiments, the system can also provide Tips 840, adding information that is parsed from the health information database but is considered more of an adjunct to the health maintenance plan. For example, the user may be provided with tips regarding stress management as it relates to personal information in the subject-profile, such as work related stress or relationship related stress at home. The system may also identify areas of interest to the subject, as derived from the subject-profile, to provide multimedia that will, for example, help reduce the stress of the subject. Such multimedia can include visuals, music, art, and the like. In some embodiments, the system can also provide Expert Info 850, which adds to the user experience by complementing the information that has thus far been obtained and parsed as higher level information through the system. In some embodiments, the user may decide that video learning is preferred and select a Video option 860 to further enhance learning experience. In these embodiments, the Video option 860 can further include several layers of hierarchy to further assist the user in the learning experience. In some embodiments, the system can also provide a tracking capability to allow the user to identify what and when changes were made to the system. This function can be labeled My Tracker 870, for example, and can be of importance to any user, including a subject, a health provider, or an administrator.

In some embodiments, the system further comprises security measures to protect the subject's privacy, integrity of data, or both. Such security measures are those well-known in the art such as firewalls, software, and the like. In addition, the system can be configured for use in an environment that requires administrative procedures and control. For example, the system can include an administrative module operable to control access, configure the engines, monitor results, perform quality assurance tests, and define audiences for targeting and trending. Since the system can safely be provided by a network and, in some embodiments, the system is coupled to a network, the security measures can help protect the contents of the system from external intrusions.

In some embodiments, the system is a web enabled application and can use, for example, Hypertext Transfer Protocol (HTTP) and Hypertext Transfer Protocol over Secure Socket Layer (HTTPS). These protocols provide a rich experience for the end user by utilizing web 2.0 technologies, such as AJAX, Macromedia Flash, etc. In some embodiments, the system is compatible with Internet Browsers, such as Internet Explorer, Mozilla Firefox, Opera, Safari, etc. In some embodiments, the system is compatible with mobile devices having full HTTP/HTTPS support, such as iPhone, Pocket-PCs, Microsoft Surface, Video Gaming Consoles, and the like. In some embodiments, the system can be accessed using a Wireless Application Protocol (WAP). This protocol will serve the non HTTP enabled mobile devices, such as Cell Phones, BlackBerries, etc., and provides a simple interface. Due to protocol limitations, the Flash animations are disabled and replaced with Text/Graphic menus. In some embodiments, the system can be accessed using a Simple Object Access Protocol (SOAP) and Extensible Markup Language (XML). By exposing the data via SOAP and XML, the system provides flexibility for third party and customized applications to query and interact with the system's core databases. For example, custom applications could be developed to run natively on iPhones, Java or .Net-enabled platforms, etc. One of skill will appreciate that the system is not limited to the platforms discussed above and will be amenable to new platforms as they develop.

Figure 9:
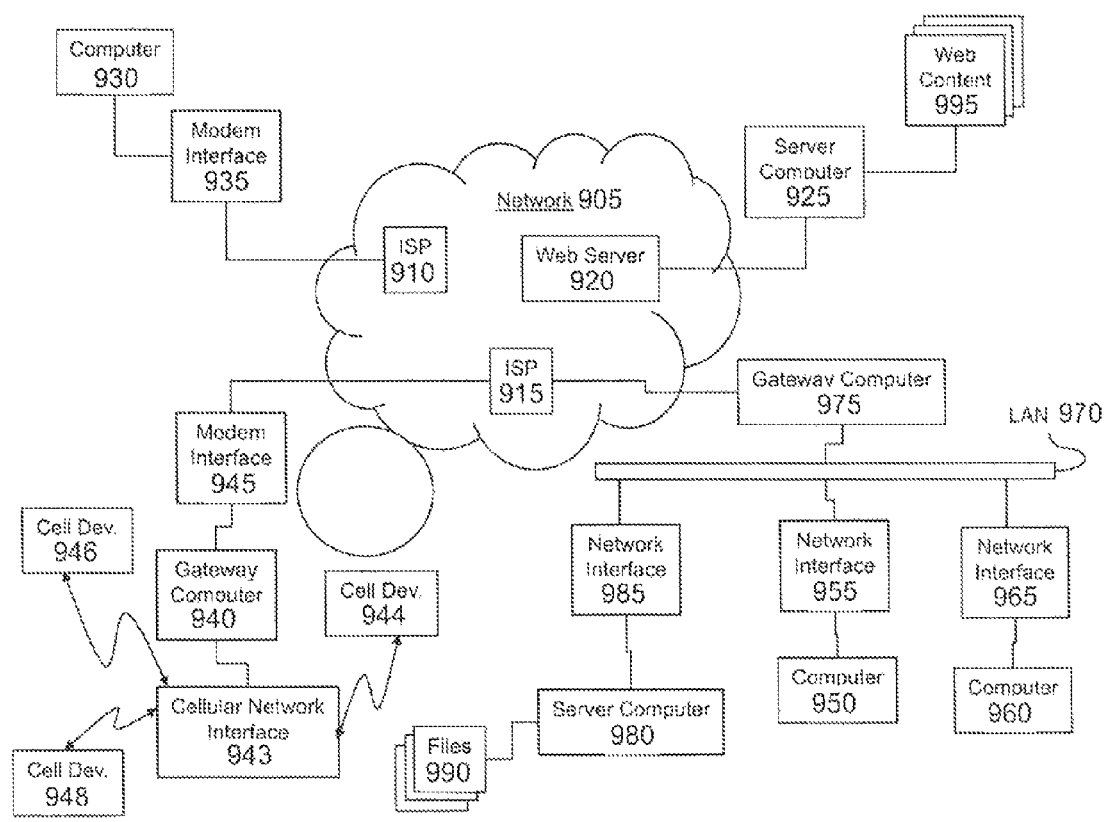
FIG. 9 shows how a network may be used for the personalized health information discovery and presentation system in some embodiments.

FIG. 9 shows how a network may be used for the personalized health information discovery and presentation system in some embodiments. FIG. 9 shows several computer systems coupled together through a network 905, such as the internet, along with a cellular network and related cellular devices. The term "internet" as used herein refers to a network of networks which uses certain protocols, such as the TCP/IP protocol, and possibly other protocols such as the hypertext transfer protocol (HTTP) for hypertext markup language (HTML) documents that make up the world wide web (web). The physical connections of the internet and the protocols and communication procedures of the internet are well known to those of skill in the art.

Access to the internet 905 is typically provided by internet service providers (ISP), such as the ISPs 910 and 915. Users on client systems, such as client computer systems 930, 950, and 960 obtain access to the internet through the internet service providers, such as ISPs 910 and 915. Access to the internet allows users of the client computer systems to exchange information, receive and send e-mails, and view documents, such as documents which have been prepared in the HTML format. These documents are often provided by web servers, such as web server 920 which is considered to be "on" the internet. Often these web servers are provided by the ISPs, such as ISP 910, although a computer system can be set up and connected to the internet without that system also being an ISP.

The web server 920 is typically at least one computer system which operates as a server computer system and is configured to operate with the protocols of the world wide web and is coupled to the internet. Optionally, the web server 920 can be part of an ISP which provides access to the internet for client systems. The web server 920 is shown coupled to the server computer system 925 which itself is coupled to web content 995, which can be considered a form of a media database. While two computer systems 920 and 925 are shown in FIG. 9, the web server system 920 and the server computer system 925 can be one computer system having different software components providing the web server functionality and the server functionality provided by the server computer system 925 which will be described further below.

Cellular network interface 943 provides an interface between a cellular network and corresponding cellular devices 944, 946 and 948 on one side, and network 905 on the other side. Thus cellular devices 944, 946 and 948, which may be personal devices including cellular telephones, two-way pagers, personal digital assistants or other similar devices, may connect with network 905 and exchange information such as email, content, or HTTP-formatted data, for example. Cellular network interface 943 is coupled to computer 940, which communicates with network 905 through modem interface 945. Computer 940 may be a personal computer, server computer or the like, and serves as a gateway. Thus, computer 940 may be similar to client computers 950 and 960 or to gateway computer 975, for example. Software or content may then be uploaded or downloaded through the connection provided by interface 943, computer 940 and modem 945.

Client computer systems 930, 950, and 960 can each, with the appropriate web browsing software, view HTML pages provided by the web server 920. The ISP 910 provides internet connectivity to the client computer system 930 through the modem interface 935 which can be considered part of the client computer system 930. The client computer system can be a personal computer system, a network computer, a web TV system, or other such computer system.

Similarly, the ISP 915 provides internet connectivity for client systems 950 and 960, although as shown in FIG. 9, the connections are not the same as for more directly connected computer systems. Client computer systems 950 and 960 are part of a LAN coupled through a gateway computer 975. While FIG. 9 shows the interfaces 935 and 945 as generically as a "modem," each of these interfaces can be an analog modem, isdn modem, cable modem, satellite transmission interface (e.g. "direct PC"), or other interfaces for coupling a computer system to other computer systems.

Client computer systems 950 and 960 are coupled to a LAN 970 through network interfaces 955 and 965, which can be ethernet network or other network interfaces. The LAN 970 is also coupled to a gateway computer system 975 which can provide firewall and other internet related services for the local area network. This gateway computer system 975 is coupled to the ISP 915 to provide internet connectivity to the client computer systems 950 and 960. The gateway computer system 975 can be a conventional server computer system. Also, the web server system 920 can be a conventional server computer system.

Alternatively, a server computer system 980 can be directly coupled to the LAN 970 through a network interface 985 to provide files 990 and other services to the clients 950, 960, without the need to connect to the internet through the gateway system 975.

Through the use of such a network, for example, the system can also provide an element of social networking, whereby users can contact other users having similar subject-profiles, or user can contact loved ones to forward the personalized information. In some embodiments, the system can include a messaging module operable to deliver notifications via email, SMS, and other mediums. In some embodiments, the system is accessible through a portable, single unit device and, in some embodiments, the input device, the graphical user interface, or both, is provided through a portable, single unit device. In some embodiments, the portable, single unit device is a hand-held device.

Regardless of the information presented, the system exemplifies the broader concept of a personalized learning tool. The system can integrate vast amounts of information derived from one or more sources into a personalized presentation of information, regardless of the content of the information—health, sports, finance, science, art, literature, etc. The system organizes information for individuals in a multi step fashion, displaying the information in easy to understand formats, and then optimizing the information so that various sub topics are personalized and interrelated.

The information can be presented in one set or parsed into multiple sets in a first layer of an information hierarchy, each set of which can be further parsed into more sets in another layer, and then again in another layer, and so on, in order to prioritize the information for the user. In this way, the user can gain a limited amount of information rather quickly and have the option of learning in more depth as the user enters each successive layer of the hierarchy. The personalized presentation of information makes learning faster and more interesting for the user. The techniques described herein can be used for any information content including, for example, health, finance, sports, science, arts, literature, languages, politics, pop culture, and the like. A user begins in a particle topic area, for example, medical, finance or education. Information is gathered on a subject, which may or may not be the user, using previously arranged templated questionnaires, answers to which populate a user plan. Such questionnaires can be, for example, demographics, survey activity, and other questions common in a particular field. Some response may also trigger more questionnaires. The user can also customize the system, such as choosing interfaces, colors, language, notifications, etc.

The system enhances learning by layering information into sets and subsets, such that the information is easier to assimilate as manageable subparts. The user is allowed to enter preferences into the system in order to customize visual displays that present the information the user in a personalized way that provides a methodology of understanding deep, coherent explanations. And, the system also enhances learning by providing contraindications, adverse interacts, or conflicts, information that would have otherwise been undiscovered by the user through conventional information gathering techniques. The system can enhance learning by providing a perceptual motor experience, and can provide a multimedia interaction for the user rather than simply providing information on a single medium, such as a display that is limited to a text display, or perhaps just a diagram or picture. In some embodiments, the multimedia interaction includes one or more of text and video; sound and diagrams, pictures, or images; sound; and video.

In some embodiments, the system can help anchor the learning process by aligning a subject's personal profile and interests in the selection of information to be displayed to the user. As such, the system can engage a user to be an active participant in self-discovery, explicitly link related ideas, and minimize material that the user may consider distracting, disinteresting, or irrelevant. The system can also function to avoid "negative suggestion effect," a term that refers to an undesirable learning effect often seen, for example, from use of multiple choice questions as a learning tool. This undesirable effect occurs when misleading answers are provided to mislead a student in multiple choice questions, and the student learns the false answers rather than the correct answers.

In general terms, the system is a paradigm shift in learning tools, providing a novel learning system that implements a personalized presentation of information to assist a user at assimilating the information. The user can be proactive in designing the presentation of information, or the user can use default settings, however the proactive approach facilitates the understanding of interconnections between multiple sets and types of information, and simplifies the assimilation of information. The information can be complex, such as information obtained from several external sources, including computer databases and websites, whether or not publicly available.

The system and its information database can include any of a variety of system libraries that contain organized sets of any of a variety of information of value to users. Moreover, can information can be obtained from external data sources, whereby plug-ins and APIs can be designed to allow integration with third party systems and exchange data with external data sources. The external data sources can be used to provide information on demand, to update existing information stored in the system libraries, or both.

Although a default presentation format can be made available, the user can design and use an interactive "visual dashboard" presented on a graphical user interface, whereby the user first designs the appearance of the dashboard and can look at general outlines of information, often vast amounts of information, and can decide how to parse and subdivide information through the user selection of solutions subsets, which are merely subsets of like data selected by the user for ease of learning. The user can interactively design summary pages, for example, wherein the user selects how the information is integrated into hierarchical layers by selecting main categories within which to place the information. Moreover, the system has an optimization function performed by an integration engine, whereby conflicting information, contraindications, and the like, can be indentified and presented to the user. The user can also ask the system to flag and display information that is identified by the system during integration and is of some particular interest to the user. The user can, for example, select parameters of interest, such as amounts, ranges, percentages, rates, lapses of time, conflicting information, contraindications due to the presence of combinations of information, or any other fact of interest to the user.

In some embodiments, the system contains an engine operable to create and optimize personalized content for users. The engine integrates information from other modules, as well as human inputs, e.g. from administrators and user interactions, and produces an optimized presentation for the user. In some embodiments, the engine can learn about the user through continued use, wherein the data collection algorithms and methods are modified to correlate with, for example, a user's types and frequencies of choices and answers. Relationships between the choices and answers can be structured to match the subject-profile, in some embodiments. In these embodiments, the engine starts with proprietary generic rules and algorithms, and these rules and algorithms continue to be refined as the system collects information and learns from the user and his/her interactions.

Some portions of the detailed description are presented in terms of operations of the system. The operations are those requiring physical manipulations of physical quantities resulting in a useful product being produced. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. All of these and similar terms are to be associated with the appropriate physical quantities and are merely convenient labels applied to these quantities. Unless specifically stated otherwise, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Moreover, the teachings relate to a system for performing the operations herein. This system may be specially constructed as an apparatus designed solely for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

It should be also appreciated that the methods and displays presented herein are not inherently related to any particular computer or other apparatus. Various general purpose systems may be used with programs in accordance with the teachings herein, or it may prove convenient to construct more specialized apparatus to perform the methods of some embodiments. The required structure for a variety of these systems will be apparent to one of skill given the teachings herein. In addition, the techniques are not described with reference to any particular programming language, and various embodiments may thus be implemented using a variety of programming languages. Accordingly, the terms and examples provided above are illustrative only and not intended to be limiting; and, the term "embodiment," as used herein, means an embodiment that serves to illustrate by way of example and not limitation. The following examples are illustrative of the uses of the present invention. It should be appreciated that the examples are for purposes of illustration and are not to be construed as limiting to the invention.

We claim:

1. A system for creating an iteratively-optimized, personalized health maintenance plan for a user, the system comprising:
 a processor
 a non-transitory computer-readable storage medium including components executable by the processor, the components comprising:
   a subject-profile component operable to provide a user with a template questionnaire for creating a personalized subject-profile, receiving answers to the questionnaire from the user for use in creating the personalized subject profile, and converting the personalized subject profile into a recognized health profile for the subject;
   a library component comprising health information and operable for use in creating an optimized-personalized health maintenance plan for the user;
   an alignment component operable for use in aligning the recognized health profile with health information from the library component that is determined by the system as relevant to the recognized health profile;
   a solutions component operable for parsing the relevant health information into information subsets;
   an integration component operable for (i) integrating information from the recognized health profile with the relevant health information; (ii) identifying any conflicting health information, contraindications, and health warnings obtained from the health information database; and (iii) compiling information comprising the integrated information and any conflicting health information, contraindications, and health warnings for presentation to the user;
   a planning component operable for converting the integrated health information compiled information into a presentation format for the first personalized health maintenance plan, or an optimized-personalized health maintenance plan;
   wherein, the system produces the iteratively-optimized personalized health maintenance plan, the plan based on at least a first iterated questionnaire provided to the user and on the answers to the template questionnaire; and,
   the optimization increases the level of specificity of the personalized health maintenance plan for the user.

2. The system of claim 1, wherein, the system further optimizes the health maintenance plan by creating one or more additional questionnaires for the user, each additional questionnaire based on answers to a preceding questionnaire.

3. The system of claim 1, wherein, the system functions to produce the optimized-personalized health maintenance plan based on an "$n^{th}$" iteration, n being an integer greater than or equal to 1;
   where n=1, a first iterated questionnaire is provided to the user and is based on the answers to a template questionnaire;
   where n>1, an additional nth questionnaire is provided to the user and is based on the answers to the $(n-1)^{th}$ questionnaire;
   and,
   the personalized health maintenance plan is optimized to the nth iteration to increase the level of specificity of the personalized health maintenance plan for the user.

4. The system of claim 1, wherein the subject-profile comprises one or more of the subject's age, sex, height, weight, known medical conditions, vital signs, laboratory test results, prior conditions, prior treatments, prescriptions, and family medical history.

5. The system of claim 1, wherein the system comprises a data exchange component operable for interacting with external medical data formats, wherein the subject-profile comprises external medical data obtained from a health provider's database.

6. The system of claim 1, wherein the health maintenance plan comprises a care management plan, a disease management plan, or both.

7. The system of claim 1, wherein the relevant health information includes the subject's activity, nutrition, stress, and sleep.

8. The system of claim 1, wherein the system comprises a security component operable for protecting the subject's privacy, integrity of data, or both.

9. The system of claim 1, wherein
   the relevant health information includes the subject's activity, nutrition, stress, and sleep;
   the solutions component parses the relevant health information into activity, nutrition, stress, and sleep;
   the alignment component aligns the library of health information with the subject's activity, nutrition, stress and sleep; and
   the planning component provides a personalized health maintenance plan comprising the four categories of activity, nutrition, stress, and sleep.

10. The system of claim 1, wherein the user is an individual producing the health maintenance plan for the subject and is selected from the group consisting of a health care provider, an insurance provider, a teacher, and an athletic coach.

11. The system of claim 1, wherein the user accesses a select subtopic from the health information; and, answers one or more additional queries generated by the system about the subtopics;
   wherein, the personalized health maintenance plan is iteratively optimized at each level of questioning to produce a health maintenance plan that is optimized by the user by subtopic.

12. A method for creating an iteratively-optimized, personalized health maintenance plan for a user, the method comprising:
   producing, using a processor, a recognized health profile for a subject, wherein the producing includes providing a user with a template questionnaire;
   obtaining answers to the questionnaire from the user, the answers used to create a personalized subject-profile for a subject; and,
   converting the personalized subject-profile into the recognized health profile for the subject using the answers to the questionnaire;
   developing, using the processor, a first personalized health maintenance plan, wherein the developing includes
      gathering health information that is relevant to the recognized health profile for the subject;
      aligning the recognized health profile with the health information;
      integrating information from the recognized health profile with the relevant health information;
      identifying any conflicting health information, contraindications, and health warnings obtained from the health information database; and,
      compiling information comprising the integrated information and any conflicting health information, contraindications, and health warnings for presentation to the user;
   and,
   converting the compiled information into a presentation format for the first personalized health maintenance plan, or an optimized-personalized health maintenance plan;
   wherein,
   the system produces the iteratively-optimized, personalized health maintenance plan based on at least a first iterated questionnaire provided to the user and based on the answers to the template questionnaire; and,
   the optimization increases the personalized health maintenance plan for the user.

13. The method of claim 12, wherein, the method further optimizes the health maintenance plan by creating one or more additional questionnaires for the user, each additional questionnaire based on answers to a preceding questionnaire.

14. The method of claim 12, wherein,
   the system functions to produce the optimized-personalized health maintenance plan based on an "$n^{th}$" iteration, n being an integer greater than or equal to 1;
   where n=1, a first iterated questionnaire is provided to the user and is based on the answers to a template questionnaire;
   where n>1, an additional nth questionnaire is provided to the user and is based on the answers to the $(n-1)^{th}$ questionnaire;
   and,
   the personalized health maintenance plan is optimized to the nth iteration to increase the level of specificity of the personalized health maintenance plan for the user.

15. The method of claim 12, wherein the subject-profile comprises one or more of the subject's age, sex, height, weight, known medical conditions, vital signs, laboratory test results, prior conditions, prior treatments, prescriptions, and family medical history.

16. The method of claim 12, wherein the method comprises exchanging information with additional external medical information obtained from a health provider's database.

17. The method of claim 12, wherein the health maintenance plan comprises a care management plan, a disease management plan, or both.

18. The method of claim 12, wherein the relevant health information includes the subject's activity, nutrition, stress, and sleep.

19. The method of claim 12, wherein the system comprises protecting the subject's privacy, integrity of data, or both.

20. The method of claim 12, wherein
- the relevant health information includes the subject's activity, nutrition, stress, and sleep;
- the method includes parsing the relevant health information into activity, nutrition, stress, and sleep;
- the method includes aligning health information with the subject's activity, nutrition, stress and sleep; and
- the method includes planning a personalized health maintenance plan comprising the four categories of activity, nutrition, stress, and sleep.

21. The method of claim 12, wherein the user is an individual producing the health maintenance plan for the subject and is selected from the group consisting of a health care provider, an insurance provider, a teacher, and an athletic coach.

22. The method of claim 12, wherein the user accesses a select subtopic of the health information; and, interactively and iteratively answers one or more additional queries about the subtopics;
- wherein, the personalized health maintenance plan is iteratively optimized at each level of questioning to produce a health maintenance plan that is optimized by the user by subtopic.

* * * * *